| United States Patent [19] | [11] Patent Number: 4,646,578 |
|---|---|
| Lawrenz et al. | [45] Date of Patent: *Mar. 3, 1987 |

[54] MOLTEN METAL SAMPLING DEVICE

[75] Inventors: Dennis A. Lawrenz, Bridgman; Ken A. Rinkenberg, Stevensville, both of Mich.

[73] Assignee: Leco Corporation, St. Joseph, Mich.

[*] Notice: The portion of the term of this patent subsequent to Feb. 17, 2004 has been disclaimed.

[21] Appl. No.: 729,169

[22] Filed: Apr. 30, 1985

[51] Int. Cl.$^4$ ............................................. G01N 1/14
[52] U.S. Cl. ............................... 73/864.52; 73/864.59
[58] Field of Search .......... 73/864.52, 864.53, 864.59, 73/DIG. 9, 864.54, 864.55, 864.56, 864.57, 864.58; 249/DIG. 4; 374/140

[56] References Cited

U.S. PATENT DOCUMENTS

| 2,139,114 | 12/1938 | Demers . | |
|---|---|---|---|
| 2,143,982 | 1/1939 | Hare et al. . | |
| 2,485,492 | 10/1949 | Hubbard et al. . | |
| 2,861,450 | 11/1958 | Ransley | 73/19 |
| 2,970,350 | 2/1961 | Feichtinger . | |
| 3,315,529 | 4/1967 | Feichtinger | 73/DIG. 9 |
| 3,369,406 | 2/1968 | Lowdermilk et al. | 73/DIG. 9 |
| 3,390,568 | 7/1968 | Taylor | 73/19 |
| 3,452,602 | 7/1969 | Hackett . | |
| 3,457,790 | 7/1969 | Hackett . | |
| 3,501,963 | 3/1970 | Collins | 73/864.53 |
| 3,534,614 | 10/1970 | Creswell . | |
| 3,967,505 | 7/1976 | Feichtinger | 73/DIG. 9 |
| 4,007,641 | 2/1977 | Kelsey | 73/DIG. 9 |
| 4,170,139 | 10/1979 | Norita et al. | 73/864.52 |
| 4,428,245 | 1/1984 | Nakamura et al. | 73/864.52 |
| 4,445,390 | 5/1984 | Atwell | 73/864.52 |
| 4,535,640 | 8/1985 | Falk | 73/864.55 |

FOREIGN PATENT DOCUMENTS

| 1922677 | 11/1970 | Fed. Rep. of Germany . | |
|---|---|---|---|
| 2035420 | 1/1972 | Fed. Rep. of Germany . | |
| 2358 | 1/1978 | Japan | 73/864.52 |
| 1460024 | 12/1976 | United Kingdom | 73/864.53 |

Primary Examiner—Stewart J. Levy
Assistant Examiner—Tom Noland
Attorney, Agent, or Firm—Price, Heneveld, Cooper, DeWitt & Litton

[57] ABSTRACT

A sampling device for obtaining samples from a molten metal bath includes a pair of concentric vitreous tubes spaced from one another and coupled to each other such that the inner tube can be readily removed once the sample is taken. The outer tube is cylindrical and includes a restriction at one end defining a circular opening smaller than an adjacent end of the inner tube for supporting the end of the inner tube.

9 Claims, 4 Drawing Figures

U.S. Patent   Mar. 3, 1987   4,646,578
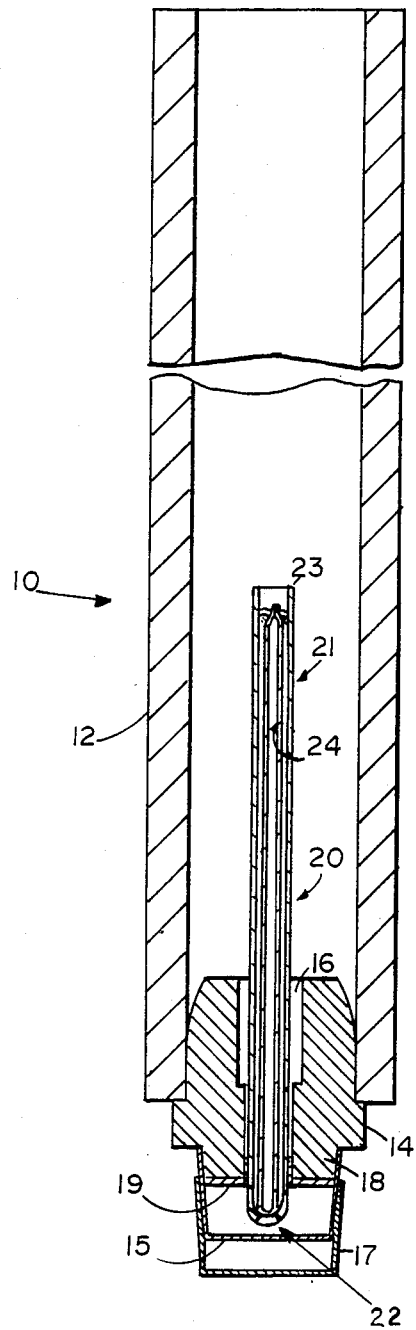
FIG. 1
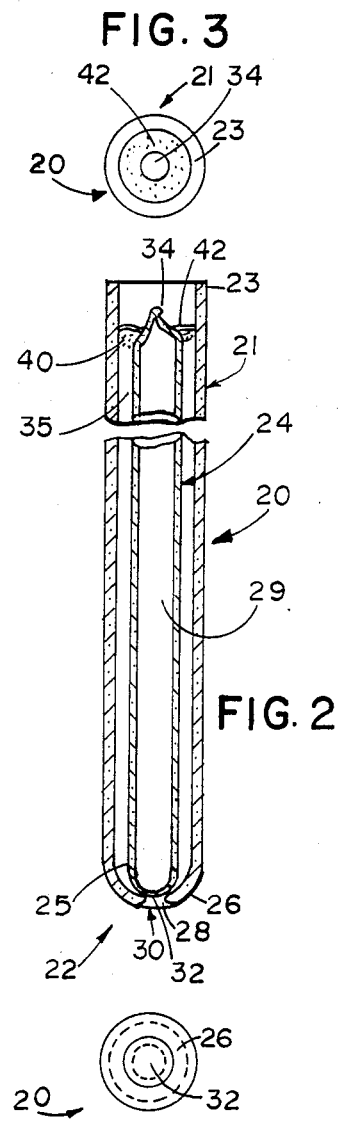
FIG. 3
FIG. 2
FIG. 4

MOLTEN METAL SAMPLING DEVICE

BACKGROUND OF THE INVENTION

The present invention pertains to an immersible molten metal sampling device and particularly to one which includes a pair of coaxial tubes made of a vitreous material.

There exists a variety of molten metal sampling devices which are immersed in a molten metal bath for example in a steel manufacturing process such that a sample of the melt can be taken to determine the contents of the melt during the steel manufacturing process. U.S. Pat. No. 4,445,390 discloses a sampling device for the removal of a sample from a molten metal bath to capture the total hydrogen content of a sample. In this and other metallic evacuated tube samplers however, the molten metal bonds to the metallic wall surfaces of the sampler and when the solid sample is analyzed therefor the resulting pin-shaped sample includes not only the molten metal desired to be analyzed but also a portion of the sampling device itself.

Glass tube samplers have been employed in the past and typically constitute a single evacuated glass tube which is immersed into the molten bath and subsequently removed and chilled first in a water bath and subsequently in liquid nitrogen in order to prevent the escape of hydrogen from the sample. Inasmuch as it is necessary to relatively rapidly chill the sample to prevent the escape of hydrogen it is necessary to quickly remove the sampling device from the sample holding tube. In the past this has been very difficult inasmuch as typically the tube is encapsulated in a ceramic material which is part of a holder as shown for example in U.S. Pat. No. 3,369,406. Naturally the longer it takes to remove the sampling device from the holder for chilling, the more free hydrogen can escape and the accuracy of the resulting analysis of the sample is adversely affected.

SUMMARY OF THE PRESENT INVENTION

The sampling device of the present invention overcomes the difficulties of the prior art sampling devices including the difficulties in rapidly handling the sample defining chamber to provide for processing of the sample as quickly as possible. The sampling device of the present invention achieves these goals by providing a pair of vitreous coaxially mounted tubes with the inner tube defining a sample receiving chamber. The outer tube defines a support member for supporting the inner tube with respect to a sample holder which is immersed into the molten metal bath. The inner tube in the preferred embodiment is evacuated with a fusable end which, when exposed to the molten metal bath, melts to admit the sample. The sampling device of the present invention also provides a sample receiving chamber or inner tube which is readily removed for either chilling or for positioning in a chamber such as described in copending U.S. patent application Ser. No. 676,782 entitled SAMPLING CELL AND METHOD filed on Nov. 30, 1984 and assigned to the present assignee and now abandoned.

These and other features, objects and advantages of the present invention will become apparent upon reading the following description thereof together with reference to the accompanying drawings in which:

BRIEF DESCRIPTION OF THE DRAWINGS

FIG. 1 is a vertical cross-sectional view of a molten metal sampling device of the present invention shown mounted in a sample holding apparatus for immersion into a molten metal bath;

FIG. 2 is an enlarged fragmentary, vertical cross-sectional view of the sampling device of the present invention;

FIG. 3 is a top plan view of the structure shown in FIG. 2; and

FIG. 4 is a bottom plan view of the structure shown in FIG. 2.

DETAILED DESCRIPTION OF THE PREFERRED EMBODIMENT

Referring initially to FIG. 1 there is shown a sampling device holder 10 which is used for supporting the molten metal sampling device 20 in position as it is immersed into a molten metal bath. In the embodiment shown device 10 is employed for taking molten metal samples from a furnace or ladle which typically includes a layer of slag on the surface. The device 10 includes an elongated cylindrical fiberboard tube 12 into which there is fitted a sample device holder element 14 comprising a plug molded of a sand and resin material which is force fitted into the lower end of tube 12. Element 14 includes a stepped cylindrical central bore 16 which receives the generally cylindrical sampling device 20 which is cemented in position in the bore such that a sample receiving end 22 projects outwardly from the holder 14 a distance of about one-half ($\frac{1}{2}$) inch. End 22 is protected by a pair of spaced steel end caps 15 and 17 which are press fit over an annular shoulder 18 of holder 14. A steel chill washer 19 covers the exposed lower annular surface of shoulder 18 to prevent the molten metal from eroding element 14 while it is immersed. For use in sampling molten material in ingots for example where there typically is no slag layer, end caps 15 and 17 are not employed. The sampling device 10 is of generally conventional construction and the sample device 20 held within holder 14 in a conventional manner by, for example, cementing the interface between the outer cylindrical portion of sampling device 20 and the bore 16 of holder 14 with a ceramic cement or hot glue. The sampling device 20 is inserted into element 14 prior to its fitting into the lower end of cardboard tube 12. Having described the overall construction of the holder for sampling device 20, the sampling device 20 is now described in detail in conjunction with the enlarged views of FIGS. 2–4.

Device 20 comprises a pair of concentric cylindrical tubes including an outer tube 21 and an inner tube 24. Inner tube 24 is evacuated and positioned within the generally cylindrical outer tube 21. Tube 21 has a first end 26 which is narrowed to define a circular opening 28 having a diameter less than the outer diameter of tube 24. The opposite or second end 23 of tube 21 is of the same diameter as the tube. Tube 24 comprises a cylindrical tube having a first end 30 which is closed in a thinner wall section 32 than the tube itself while the second or opposite end 34 of the tube is sealed off while a vacuum is drawn on the tube by a conventional glass blowing process. Thus, tube 24 is evacuated to subatmospheric pressure. This is done and tube 24 is held in concentric relationship within tube 21 with end 30 in abutment against the inner annular shoulder 25 of tube 21 surrounding aperture 28. A commercially available ceramic fiber packing material 40 is placed around opposite end 34 of tube 24 and in the annular space 35 between the tubes to support the free end 34 of tube 24 in concentric relationship with end 23 of the outer tube. Subsequently a thin layer of ceramic cement 42 such as Sauereisen cement is applied to the outer annular surface of the ceramic fiber material 40 to hold the fiber material in place. The combination of the fibrous material and ceramic cement thus define a frangible interconnection of tubes 21 and 24 at ends 23 and 34 respectively. The inner tube defines a sample receiving chamber which can be readily removed once a sample is taken since a cylindrical air space 35 extends between the tubes.

In use, sampling device 20 is inserted in the holder 10 as described above and the relatively thin end 32 of the quartz inner tube 24 melts upon immersion in the molten metal bath allowing the evacuated tube to draw molten metal material into its inner pin sample defining cavity 29. The interface between end 30 of tube 24 and shoulder 25 of tube 21 is sufficiently tight to prevent molten metal from entering the cylindrical space 35 which also is prevented by the utilization of the ceramic packing material 40 and cement 42 from the open end 23 of tube 21. Once a sample has been taken, tube 24 is removed by fracturing end 22 which at the same time frees end 34 of the tube. This is typically achieved by mechanically rapping the lower end of the sample holder 10 against a hard surface or alternatively by utilizing pliers to snap off end 22.

In the preferred embodiment of the device shown in FIGS. 2-4, vitreous outer tube 21 was an 11 millimeter outer diameter quartz tube while vitreous tube 24 was an 8 millimeter outer diameter quartz tube each tube having a wall thickness of approximately 1 millimeter and a length of about 6 inches. Sampling device 20 is broken near the tip end 26 for removal of the inner tube 24. During the breaking process the frangible connection at the opposite end 23 also breaks such that tube 24 can be readily removed from the broken lower end of tube 21 for handling of the pin sample contained therein. The thickness of end 32 of tube 24 is about 0.0015 inches and is formed by a conventional glass blowing technique. Tube 24 is evacuated to a pressure of approximately 100 microns (0.1 mmHg) during its manufacturing to provide the evacuated mold defining chamber. Although in the preferred embodiment the tubes are made of quartz, it would be possible to make the tubes of other suitable vitreous material as long as a frangible interconnection was provided such that the inner tube could be quickly and readily removed from the outer tube by fracturing at least the outer tube.

Various modifications to the preferred embodiments of the invention will become apparent to those skilled in the art but will fall within the spirit of scope of the invention as defined in the appended claims.

The embodiments of the invention in which an exclusive property or privilege is claimed are defined as follows:

1. A sampling system for sampling molten metal comprising:
   a first cylindrical tube made of a vitreous material;
   a second cylindrical tube made of a vitreous material and evacuated and sealed at opposite ends, said second tube substantially coextensive with said first tube and having an outer diameter less than the inner diameter of said first tube such that it can be positioned within said first tube and wherein one end of said second tube is fusible when immersed in molten metal for admitting molten metal into said second tube; and
   means for coaxially mounting said second tube within said first tube wherein said first tube has first and secnd opposite ends and wherein said means for coaxially mounting said second tube within said first tube comprises a restriction formed at said first end of said first tube, said restriction defining a circular opening having a diameter less than the outer diameter of said second tube.

2. The apparatus as defined in claim 1 wherein said second tube includes first and second opposite ends and wherein said first end is sealed with a fusible generally hemispherical member having a wall thickness substantially thinner than that of the cylindrical side wall of said second tube and said second tube is positioned within said first tube with said hemispherical member adjacent said first end of said first tube.

3. The apparatus as defined in claim 2 wherein said means for coaxially mounting said tube within said first tube further includes a ceramic packing material surrounding said second end of said second tube and filling the annular space between said first and second tubes near the second ends of said tubes.

4. The apparatus as deined in claim 3 wherein said vitreous material is quartz.

5. The apparatus as defined in claim 4 wherein said means for coaxially mounting said first tube within said second tube further includes ceramic cement applied to said ceramic packing material on a side proximate said second ends of said tubes.

6. A sampling device comprising:
   a first generally cylindrical tube of vitreous material having a first hemispherically enclosed fusible end having a wall thickness substantially thinner than that of the cylindrical side wall of said first generally cylindrical tube and a sealed opposite end, said first tube evacuated to subatmospheric pressure;
   a second generally cylindrical tube of vitreous material having an inner diameter greater than the outer diameter of said first tube, said second tube having a first end which is restricted to define a circular opening having a diameter less than that of said hemispherically enclosed end of said first tube, said first tube positioned within said second tube with said hemispherically enclosed end engaging said first end of said second tube; and
   means for supporting said sealed opposite end of said first tube to said second tube such that said first tube is generally coaxial with said second tube and can be removed therefrom when said restricted end of said second tube is fractured.

7. The apparatus as defined in claim 6 wherein said vitreous material is quartz.

8. The apparatus as defined in claim 7 wherein said means for supporting said sealed opposite end comprises a ceramic packing material surrounding said first tube.

9. The aparatus as defined in claim 8 wherein said means for supporting said sealed opposite end further includes a layer of ceramic cement coating an outer surface of said packing material.

* * * * *